United States Patent [19]
Langer et al.

[11] Patent Number: 5,962,365
[45] Date of Patent: Oct. 5, 1999

[54] PROCESS FOR THE MANUFACTURE OF AROMATIC AMINES BY GAS-PHASE HYDROGENATION AND CATALYST USEFUL THEREOF

[75] Inventors: Reinhard Langer; Hans-Josef Buysch, both of Krefeld; Ursula Pentling, Duisburg, all of Germany

[73] Assignee: Bayer Aktiengesellschaft, Leverkusen, Germany

[21] Appl. No.: 08/878,592

[22] Filed: Jun. 19, 1997

Related U.S. Application Data

[62] Division of application No. 08/660,622, Jun. 6, 1996, Pat. No. 5,679,858.

[30] Foreign Application Priority Data

Jun. 14, 1995 [DE] Germany .......................... 195 21 587

[51] Int. Cl.$^6$ .............................. B01J 21/18; B01J 23/00; B01J 23/42; C07C 5/10
[52] U.S. Cl. .......................... 502/180; 502/325; 502/339; 502/185; 502/349; 585/269
[58] Field of Search .................... 502/180, 325, 502/339, 349, 185; 585/269

[56] References Cited

U.S. PATENT DOCUMENTS

| | | | |
|---|---|---|---|
| 2,285,277 | 6/1942 | Henke et al. | 502/185 |
| 2,681,938 | 6/1954 | Lindlar | 502/339 |
| 2,823,235 | 2/1958 | Graham et al. | 502/185 |
| 3,132,180 | 5/1964 | Hort et al. | 502/339 |
| 3,136,818 | 6/1964 | Sperber et al. | 564/420 |
| 3,265,636 | 8/1966 | Spiegler | 502/185 |
| 3,657,265 | 4/1972 | Kober et al. | 502/339 |
| 3,666,813 | 5/1972 | Hindin et al. | 260/580 |
| 3,804,779 | 4/1974 | Kent et al. | 502/185 |
| 3,882,048 | 5/1975 | Thelen et al. | 252/464 |
| 4,265,834 | 5/1981 | Birkenstock et al. | 564/421 |
| 4,366,325 | 12/1982 | Wedemeyer et al. | 502/215 |
| 5,235,106 | 8/1993 | Didillon et al. | 564/417 |
| 5,304,525 | 4/1994 | Immel et al. | 502/185 |

FOREIGN PATENT DOCUMENTS

| | | | |
|---|---|---|---|
| 2155563 | 9/1996 | Canada | C07C 211/44 |
| 476404 | 3/1992 | European Pat. Off. | C07C 209/36 |

*Primary Examiner*—Mark L. Bell
*Assistant Examiner*—Patricia L. Hailey
*Attorney, Agent, or Firm*—Joseph C. Gil; Lyndanne M. Whalen

[57] ABSTRACT

Aromatic amines are produced by catalytic hydrogenation of nitroaromatic compounds in the gas phase. The catalyst includes palladium and lead on graphite or on a graphite-containing coke support. From 30 to 6000 equivalents of hydrogen for each equivalent of nitro groups are contacted with the catalyst during this process.

3 Claims, No Drawings

5,962,365

PROCESS FOR THE MANUFACTURE OF AROMATIC AMINES BY GAS-PHASE HYDROGENATION AND CATALYST USEFUL THEREOF

This application is a division of application Ser. No. 08/660,622 filed Jun. 6, 1996, now U.S. Pat. No. 5,679,858.

BACKGROUND OF THE INVENTION

The present invention relates to an improved process for the manufacture of aromatic amines by catalytic hydrogenation of nitroaromatics in the gas phase and to a new catalyst useful in this process.

Anilines are important intermediate products for the manufacture of dyestuffs, polyurethanes and plant-protection products.

Various methods for hydrogenation of nitrobenzene and other nitroaromatics are known. Due to the large enthalpy of reaction released during these known processes, all are carried out in reactors having integrated heat-carrier systems. For example, hydrogenation in liquid phase on a suspended catalyst (e.g., Pd catalyst) is described in EP 476,404. Hydrogenation in the gas phase on a fluidized solid catalyst is disclosed, for example, in U.S. Pat. No. 3,136,818. Hydrogenation in the gas phase on a stationary catalyst (e.g., a supported Pd catalyst) is described in DE-A 2,244,401; 2,849,002; and 4,039,026.

In DE-A 2,244,401 and 2,849,002, Pd catalysts on aluminum oxide supports that can be operated as stationary catalyst beds in heat-exchanger tubes under normal pressure at loadings of less than 1 g nitrobenzene (Nbz)/ml catalyst h with low hydrogen/nitrobenzene ratios are described. Between 6 and 11 moles of hydrogen per mole of nitrobenzene are fed into the reactor. These catalysts must be regenerated approximately every 1000 hours. Each of the described processes is operated in a Gas Hourly Space Velocity (GHSV) range between 600 and 900 h$^{-1}$.

In DE-A 4,039,026, Pd catalysts on graphitic supports are described. The process described in this disclosure is carried out under conditions similar to those used for processes in which Pd catalysts on aluminum oxide are used. At loadings clearly below 1 g (Nbz)/ml catalyst h and a hydrogen/nitrobenzene ratio of 14–26 moles to 1 mole, the catalysts show incomplete conversion. Between 1000 and 4000 ppm nitrobenzene, relative to aniline formed, are found in the condensate. The selectivities relative to aniline vary between 99.1 and 99.6%. The process is described for a GHSV range between about 2000 and 3150 h$^{-1}$.

Both an increase of the nitroaromatic loading and a raising of the hydrogen/nitroaromatic ratio raise the volumetric flow rate through the catalyst bed thus reducing the residence time on the catalyst. Both measures should therefore lead to an increase of the nitroaromatic breakthrough (i.e., incomplete conversion).

A general measure of this gas flow through the catalyst bed is the Gas Hourly Space Velocity (GHSV), quoted in the unit h$^{-1}$.

However, even small amounts of nitroaromatics in aromatic amines lead to distinct discoloration of the otherwise colorless aromatic amine and are therefore undesirable. Removal of the nitroaromatics by distillation is demanding, both with respect to the apparatus and to the amount of energy consumed.

In each of these process variants, the large heat of reaction generated must be withdrawn from an industrial reactor via a complicated heat carrier system.

Hydrogenation processes in the gas phase with simple adiabatic catalyst beds are particularly economical because simple apparatus without an integrated heat exchanger system may be used. However, the large exothermicity of nitro group hydrogenation means that special requirements for the catalyst must be met. The catalyst must hydrogenate selectively over a wide temperature range. In the adiabatic process, a heat carrier (in hydrogenation processes this carrier is usually hydrogen) is also admixed with the educt mixture which leads to very short residence times (i.e., large GHSV's). The catalyst must therefore, in addition to its selectivity over a wide temperature range, be very active in order to obtain a complete nitrobenzene conversion, even at low nitrobenzene loadings.

SUMMARY OF THE INVENTION

It is an object of the present invention to provide a catalyst with a higher loadability than the known catalysts, i.e., a catalyst which shows complete conversion at large GHSVs and which can be used in simple reactor structures.

It is also an object of the present invention to provide a process for producing aromatic amines which achieves continuously high selectivities from the startup of the catalyst to its deactivation, so that an expensive working-up by distillation of the aromatic amine condensate with elaborate apparatus is not necessary.

It is another object of the present invention to provide a process for producing aromatic amines which can be carried out with unexpectedly long on-line times and high selectivities.

These and other objects which will be apparent to those skilled in the art are accomplished by hydrogenation of a nitroaromatic compound in the gas phase in the presence of palladium-lead catalyst on a graphite or graphitic carbon support and a large excess of hydrogen. Heat may be removed from the catalyst bed by means of an optional heat carrier system. Simple adiabatic reactor constructions which until now could not be used for nitrobenzene hydrogenation are adequate. The continuously high selectivity of this process makes an elaborate working-up of the condensed aromatic amine by distillation unnecessary.

DETAILED DESCRIPTION OF THE PRESENT INVENTION

The present invention relates to a process for the production of an aromatic amine represented by the formula

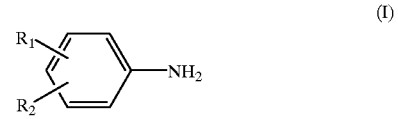

(I)

in which

R$^1$ and R$^2$, independently of each other, represent hydrogen, a methyl group or an ethyl group, and R$^1$ can also represent an amino group, by hydrogenation of a nitroaromatic compound represented by the formula

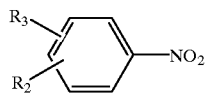

(II)

in which

R² and R³, independently of each other, represent hydrogen, a methyl group or an ethyl group, and R³ may also represent a nitro group, with hydrogen on a stationary catalyst in the gas phase. The catalyst is made up of palladium and lead on graphite or a graphite-containing coke support which has a BET surface area of 0.2 to 10 m²/g. The catalyst has a palladium content, relative to the total weight of the catalyst, of from 0.001 to 7 wt. %, preferably from 0.1 to 6 wt. %, more preferably from 0.5 to 5 wt. %, most preferably from 1.5 to 4 wt. %, and a lead content of preferably from 80 to 1000, most preferably from 100 to 300 equivalents of hydrogen per equivalent of nitro groups are fed to the catalyst.

The present invention also relates to a catalyst on a support of graphite or graphite-containing coke which has a BET surface area of from 0.2 to 10 m²/g, a palladium content (applied by impregnation) of from 0.001 to 7 wt. %, relative to the total weight of the catalyst, and a lead content of from 0.1 to 50 wt. %, preferably from 0.2 to 30 wt. %, relative to the palladium content.

Graphite-containing materials are used as support material for the manufacture of the catalysts. Examples of suitable graphites are electrographite and cokes, such as needle coke or petroleum coke. These supports generally have BET surface areas of from 0.2–10 m²/g.

The catalyst of the present invention may be prepared by applying palladium and lead separately or together to the support in from 1 to 50, preferably from 2 to 30, most preferably from 4 to 10 impregnation steps. Between each impregnation step, the catalyst support is dried in a hot gas stream, preferably an air or nitrogen stream. Between palladium and lead impregnations, the palladium can be reduced, e.g. with hydrogen.

The catalysts of the present invention may be produced by applying the palladium in the form of a suitable salt to the support which is in the form of tablets, spheres, granules, Raschig rings, Pall rings, cart wheels, or honeycomb structures of 1 to 30 mm diameters. When prepared by this method, several impregnation steps can be carried out with drying after each application. The drying is carried out in an air stream at temperatures of from 30 to 140° C., preferably at 30 to 60° C., preferably at normal pressure. Aqueous and organic solvents as well as mixtures thereof may be used for the impregnation of the support. Suitable solvents include: water, NH₃, simple alcohols, amines, ketones, esters, cyclic ethers, halogenated hydrocarbons and nitriles. Specific examples of suitable organic solvents are methanol, ethanol, propanol, isopropanol, methylamine, ethylamine, isopropylamine, acetone, methyl ethyl ketone, dioxane, methylene chloride, acetonitrile and comparable solvents. Suitable palladium salts include palladium chloride, palladium nitrate, palladium acetylacetonate, palladium acetate and amine complexes of palladium. The catalysts are preferably prepared in the absence of any halogen-containing solvent and metal salt.

Organic and inorganic lead compounds can be used to prepare the catalysts of the present invention. Suitable organic lead compounds include, for example, lead tetraalkyl compounds such as tetraethyl lead. Suitable lead salts include: lead chloride, lead nitrate and lead acetate. The catalyst is preferably prepared in the absence of any halogen-containing solvent or metal salt. After the impregnation and the final drying, the catalyst of the present invention is ready.

Before use, the catalyst may be activated by treating it with a hydrogen stream of from 1 to 10 bar at temperatures of from about 250 to about 450° C., preferably from 300 to 400° C., for from about 1 to about 50 hours, preferably from 5 to 30 hours.

The hydrogenation process of the present invention is generally carried out at a pressure of from about 1 to about 30 bar, preferably from about 1 to about 15 bar, most preferably from 1 to 7 bar.

Before the catalyst bed, the educt gas mixture containing nitroaromatic compound and hydrogen has a temperature of from about 200 to about 400° C., preferably from about 230 to about 370° C., most preferably from 250 to 350° C. The maximum catalyst temperature is 600° C., preferably 550° C., more preferably 500° C., most preferably 460° C.

The catalyst of the present invention may be used in reactors which do not have a system for heat removal.

The low residence times (i.e., high GHSVs) of the process of the present invention permit catalyst loadings of from 0.05 to 20 kg, preferably from 0.1 to 10 kg of nitroaromatic compound per liter catalyst and hour. Such residence times are considered to be remarkable.

The process of the present invention is distinguished by the absence of a catalyst startup phase and initial selectivities above 99.7%, which after a short time reach and exceed 99.9%.

Another important advantage of the process of the present invention is the quantitative conversion of the nitroaromatic compound which, surprisingly and unexpectedly, is reached even at short residence times or high GHSVs.

In the process of the present invention, the conversion of the nitroaromatic compound is generally greater than 99.95%, preferably more than 99.99%, more preferably more than 99.995%, most preferably more than 99.999%. It is, of course, possible to select process parameters which will result in lower conversions, if desired.

The catalysts of the present invention may be used in any desired reactor having a stationary catalyst bed.

In one embodiment of the present invention, the catalyst is stationary and is used in any one of the known adiabatic reactors. See, e.g., Ullmann's *Encyclopedia of Industrial Chemistry*, 4th Edition, Vol. 3, pages 468–649; and Kirk-Othmer, *Encyclopedia of Chemical Technology*, Vol. 19 (1982), pages 880–914) for descriptions of such known reactors. The catalyst bed may, however, also be distributed over several reactors which are coupled in series or parallel. Examples of such reactors are those known to be useful for the oxidation of methanol to formaldehyde.

The catalyst beds may be put on or between walls which are permeable to gas. Care must, however, be taken to ensure that gas distribution is sufficient. The catalyst may also be prepared and used on suitable packings as support material instead of in beds.

Fresh nitroaromatic compound is metered into the circulating gas stream, which mainly consists of recycled and freshly added hydrogen, before the catalyst bed. It is preferred that the nitroaromatic compound be completely vaporized in the fresh hydrogen and then added as a gas to the circulating gas stream. After passage through the catalyst bed, the product gas is cooled with steam recovery. Steam recovery may be accomplished using any of the known heat exchangers. The product gas is thereafter cooled in order to remove aromatic amine and water of reaction from the reaction mixture by condensation. The remaining circulating gas, after diverting a small amount of gas for the removal of gaseous components in the circulating gas, is recycled. Before recycling, the circulating gas and fresh educt must be preheated in admixture to inlet temperature.

The process of the present invention is particularly suitable for hydrogenating nitrobenzene and nitrotoluene.

The process of the present invention permits high catalyst loadings or GHSVs which exceed those of prior art processes. Moreover, the catalysts of the present invention make it possible to achieve selectivities above 99.7% with complete conversion at the start of the reaction. These selectivities are the highest known to be achieved for the gas-phase hydrogenation of nitroaromatic compounds. These high selectivities make it unnecessary to work-up the condensed aromatic amine by distillation.

The present invention is further illustrated but is not intended to be limited by the following examples in which all parts and percentages are parts by weight and percentages by weight, unless otherwise specified.

EXAMPLES

GHSV (Gas Hourly Space Velocity) indicates the hourly space velocity of a gas under normal conditions or at the quoted pressure relative to the empty volume which the catalyst bed occupies.

Catalyst Preparation

Granular graphite EG 17 which is commercially available from the Ringsdorff company, having a BET surface area of 0.4–0.8 m$^2$/g was used as support material for each of the catalysts used in these Examples. The grain size of this graphite was between 1 and 3 mm.

Other graphites and graphite-containing materials with small BET surface area when used as support materials for the catalysts of the present invention will, of course, produce similar results.

Each of the catalysts used in these Examples was prepared in the following manner:

Granular graphite EG 17 (1–3 mm granules, tap density 650–1000 g/l) with an absorbency of 7 ml acetonitrile per 100 g support was charged to a rotatable vessel. A solution of palladium acetate in acetonitrile was added during rotation. This mixture was kept moving until the solution was completely absorbed by the support. The solid was then dried for 5 minutes in a rapidly rising stream of air at 40° C. The impregnating and drying steps were repeated until the desired amount of palladium had been applied.

Thereafter, impregnations and dryings were carried out in the same way with aqueous lead acetate trihydrate solution until the desired amount of lead had been applied.

The dried catalyst was then activated in a hot hydrogen stream at normal pressure.

Example 1

Catalyst 1 (2% Pd, 0.5% Pb on EG 17) was prepared as described above using:

2000 g support 9 impregnations, each with 9.25 g PdAc$_2$ in 140 g acetonitrile and 2 impregnations, each with 18 g PbAc$_2$.3H$_2$O in 130 g water and was then activated for 20 h at 370° C.

Example 2 (Comparative)

Catalyst 2 (comparative catalyst without lead, 2% Pd on EG 17) was prepared using:

2000 g support and 9 impregnations, each with 9.25 g PdAc$_2$ in 140 g acetonitrile and then activated for 20 h at 370° C.

Example 3

220 ml (219.0 g) of Catalyst 1 (prepared in Example 1), with 2.0% Pd and 0.5% Pb were introduced, with a bed height of 180 mm, into a very well insulated reactor. The reactor was provided at its upper end with an evaporator and superheater. For the continuous discharge of the product gas, a well insulated tube was connected at the reactor outlet. This well insulated tube led the product into a system of tube-bundle and coiled-tube condensers for the purpose of condensation. The temperature before, in and after the catalyst bed was measured by means of a sliding thermocouple. The catalyst was first treated at normal pressure in the reactor for 10 hours at 200° C. with hydrogen being supplied via an evaporator and a superheater. Thereafter, the hydrogen stream was adjusted to 1620 l/h. At a starting temperature of $T_{init}$=202° C., 110 g/h nitrobenzene were metered by means of a metering pump via the evaporator-superheater into the hydrogen stream. This corresponded to a molar hydrogen/nitrobenzene ratio of 81/1 which at quantitative conversion under adiabatic conditions would lead to a temperature difference between educt gas stream and product gas stream of about 200° C. After a few hours, a temperature profile established itself in the catalyst bed. This profile corresponded to a heat loss via the reactor wall of approximately 10%. The rest of the heat of reaction left the catalyst bed with the product gas mixture. The gas-chromatographic analysis of the condensate yielded the results indicated in the following Table. After 3000 h, the catalyst showed no signs whatever of deactivation.

GHSV=7460 h$^{-1}$

| Running time, h | Catalyst No. | Nbz* ppm | Selectivity % | $T_{init}$ ° C. | $T_{max}$ ° C. |
| --- | --- | --- | --- | --- | --- |
| 6 | 1 | 0 | 99.88 | 202 | 385 |
| 129 | 1 | 0 | 99.90 | 202 | 385 |
| 983 | 1 | 0 | 99.94 | 202 | 386 |
| 1804 | 1 | 0 | 99.93 | 202 | 383 |
| 2912 | 1 | 0 | 99.95 | 202 | 384 |

*Nbz = Nitrobenzene

The continuously high selectivity exceeding 99.85% permitted the condensed aniline to be used without further working-up. The purity of the product can optionally be raised further by partial condensation which will reduce the proportions of low- and high-boiling by-products to less than 0.12%. It is therefore possible to avoid an expensive working-up by distillation.

Example 4 (Comparative Example with Lead-Free Catalyst)

The procedure of Example 3 was repeated using the same reactor with the exception that 220 ml (223 g) of Catalyst 2 with 2.0% Pd (prepared in Example 2) was employed. After hydrogen treatment, the metering of nitrobenzene was begun at a starting temperature of $T_{init}$=201° C. After 40h, an aniline selectivity of 99.5% was obtained at quantitative conversion. After 170 h, the selectivity to aniline had risen to more than 99.6%. After 1000 h, the catalyst showed no sign of the start of deactivation. The results of this Example are presented in the following Table.

GHSV=7460 h$^{-1}$

| Running time, h | Catalyst No. | Nbz* ppm | Selectivity % | T$_{init}$ ° C. | T$_{max}$ ° C. |
|---|---|---|---|---|---|
| 40 | 2 | 0 | 99.49 | 207 | 376 |
| 214 | 2 | 0 | 99.63 | 206 | 375 |
| 1004 | 2 | 0 | 99.73 | 207 | 377 |

*Nbz = Nitrobenzene

Under otherwise identical conditions, use of Catalyst 2 resulted in more than 400% more by-products than Catalyst 1.

Example 5 (Comparative)

The procedure of Example 3 was repeated using the same reactor, with the exception that 220 ml of a catalyst prepared in accordance with the procedure described in Example 1 of DE 2,849,002, was used. This catalyst was composed of 9 g Pd, 9 g V, and 3 g Pb on α-aluminum oxide (SPH 512 commercially available from the Rhône Poulenc Company). After activation and hydrogenation under the same conditions used in Example 3, the following results were obtained:

GHSV=7460 h$^{-1}$

| Running time, h | Nbz* ppm | Selectivity % | T$_{init}$ ° C. | T$_{max}$ ° C. |
|---|---|---|---|---|
| 3.5 | 0 | 98.8 | 199 | 383 |
| 90 | 0 | 99.1 | 195 | 372 |
| 160 | 100 | 99.6 | 200 | 375 |

*Nbz = Nitrobenzene

In an oil-heated tubular reactor at the same nitrobenzene loading and a hydrogen/nitrobenzene ratio of 6/1 (GHSV=637 h$^{-1}$), this catalyst showed a life of about 1000 h and a selectivity averaging about 99.8% over the conversion cycle.

This catalyst is therefore unsuitable for operation with large hydrogen excess and large nitrobenzene loading. The selectivities obtained were clearly lower than those achieved with the process of the present invention.

The following Examples 6 and 7 were carried out using about 2 L of Catalyst 1 at normal pressure in oil-heated heat-exchanger tubes of V2A having a conventional length of about 300 cm and an internal diameter of about 3 cm.

The loading was 0.65 g/ml h and the temperature of the heat transfer medium was adjusted to 250° C.

Example 6

GHSV=9707 h$^{-1}$

H$_2$/Nbz=81/1 Catalyst life>5000 h (no nitrobenzene breakthrough)

Example 7 (Comparative)

GHSV=2131 h$^{-1}$ (small hydrogen excess)

H$_2$/Nbz=17/1 Catalyst life 108 h (nitrobenzene breakthrough>100 ppm)

Despite a clearly smaller gas loading or GHSV, Catalyst 1 deactivated more rapidly in Example 7 than in Example 6. It is therefore apparent that below a critical hydrogen-to-nitrobenzene ratio, progressive catalyst deactivation occurs.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A catalyst suitable for hydrogenating nitroaromatic compounds on a graphite or graphite-containing coke support having a BET surface area of from 0.2 to 10 m$^2$/g which is impregnated with from 0.001 to 7% by weight palladium, based on total weight of the catalyst, and from 0.1 to 50% by weight lead, based on the weight of palladium.

2. The catalyst of claim 1 in which the support is impregnated with the palladium by applying a palladium-containing solution to the support in from 1 to 50 impregnation stages and drying the catalyst support between each application with a hot gas stream.

3. The catalyst of claim 1 in which the catalyst is activated in a hydrogen stream at 1 to 10 bar and at temperatures of from 250 to 450° C.

* * * * *